United States Patent
Whitlock (10) Patent No.: US 7,101,701 B2
(45) Date of Patent: Sep. 5, 2006

(54) METHOD TO REDUCE CONTAMINATION WHEN CULTURING MYCOBACTERIA

(75) Inventor: Robert H. Whitlock, Kennett Square, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/245,666

(22) Filed: Oct. 7, 2005

(65) Prior Publication Data

US 2006/0078979 A1    Apr. 13, 2006

Related U.S. Application Data

(60) Provisional application No. 60/617,008, filed on Oct. 8, 2004.

(51) Int. Cl.
*C12Q 1/02* (2006.01)
(52) U.S. Cl. .................. 435/253.1; 435/29; 435/253.6
(58) Field of Classification Search ............. 435/253.1, 435/253.6
See application file for complete search history.

(56) References Cited

U.S. PATENT DOCUMENTS

| | | | | |
|---|---|---|---|---|
| 5,658,749 | A | * | 8/1997 | Thornton ...................... 435/29 |
| 6,300,061 | B1 | | 10/2001 | Jacobs, Jr. et al. .............. 435/6 |
| 6,599,691 | B1 | | 7/2003 | Ralls et al. ..................... 435/4 |
| 6,664,096 | B1 | | 12/2003 | Zhang ......................... 435/243 |
| 6,841,159 | B1 | | 1/2005 | Simonson ................... 424/248 |
| 2003/0175207 | A1 | | 9/2003 | Olstein et al. .............. 424/1.49 |
| 2004/0224348 | A1 | | 11/2004 | Brentano et al. ............... 435/6 |
| 2005/0014932 | A1 | | 1/2005 | Imboden et al. ............. 530/350 |
| 2005/0100914 | A1 | | 5/2005 | Brentano et al. ............... 435/6 |
| 2005/0100915 | A1 | * | 5/2005 | Brentano et al. ............... 435/6 |

OTHER PUBLICATIONS

Bannantine et al., *J. Clinical Microbiol.* 42:106-114 (2004).
Breukink et al., *Biochem.* 37:8153-8162 (1998).
Cole et al., *Nature* 393:537-544 (1998).
Crossley et al., *Vet. Microbiol.* 107: 257-263 (2005).
Dargatz et al., *J Am. Vet. Med. Assoc.* 218 (7): 1163-1166 (2001).
Dargatz et al., *J Am. Vet. Med. Assoc.* 219 (4): 497-501 (2001).
Dimareli et al., *Australian Veterinary J* 79 (1): 47-50 (2001).
Dundee et al., *Letters in Applied Microbiology* 33 (3): 173-177 (2001).
Eda et al., *Foodborne Pathog. Dis.* 2(3):250-62 (2005).
Englund et al., *Veterinary Microbiolog.* 81 (3): 257-271 (2001).
Garnier et al., *PNAS* 100(13):7877-82 (2003).
Hughes et al., *J. Microbiol. Methods* 44 (3): 209-215 (2001).
Kuipers et al., *J. Biol. Chem.* 267:34; 24340-24346 (1992).
Kuipers et al., *Antonie van Leeuwenhock* 69:161-170 (1996).
Leite et al., *Mem. Inst. Oswaldo Cruz*, Rio de Janeiro 93:801-805 (1998).
Mason et al., *Australian Veterinary Journal* 79 (7): 497-500 (2001).
Metchock, et al., *Mycobacterium*, p. 399-437.
Nielsen et al., *J Vet Diagn Invest.* 13 (2)164-166 (2001).
Paustian et al., *J. Clinical Microbiol.* 42:2675-2681 (2004).
Sahl et al. *Ann. Rev. Microbiol.* 52:41-49 (1998).
Sasahara et al., *Abstracts of the General Meeting of the American Society for Microbiology* 101: 576 (2001).
Sauton, *C. R. Acad. Sci.* 155:860 (1912).
Stabel et al., *J. Vet. Diagn. Invest.* 16(1):22-30 (2004).
Strommenger et al., *FEMS Microbiology Letters* 196 (1): 31-37 (2001).
Thornton et al., *J. Clin. Microbiol.* 40(5):1783-90 (2002).
Van Kraaj et al., *Eur. J. Biochem.* 247:114-120 (1997).
Whitlock et al., "Fecal Culture Protocol for Mycobacterium paratuberculosis: a recommended procedure" In: *Proceedings of the 94th U.S. Animal Health Association*, Denver, CO, pp. 280-285 (1994).
Whitlock et al., *Vet Microbiol.* 77(3-4):387-98 (2000).

* cited by examiner

*Primary Examiner*—Herbert J. Lilling
(74) *Attorney, Agent, or Firm*—Evelyn H. McConathy; Drinker, Biddle & Reath LLP (57) ABSTRACT

Provided is a method for culturing *Mycobacteria* in the presence of a class A lantibiotic, thereby inhibiting or reducing bacterial contamination in the culture, without significantly disadvantageously affecting or retarding mycobacterial growth. Further provided are the *Mycobacteria* culture produced thereby, methods for detecting *Mycobacteria* in a biological sample under conditions that reduce bacterial contamination, and for diagnosing a mycobacterial infection in a biological sample from a subject suspected of having such an infection, as well as, kits useful in practicing such methods.

9 Claims, 1 Drawing Sheet

FIGURE 1

SEQUENCE LISTING

```
<160> NUMBER OF SEQ ID NOS: 1

<210> SEQ ID NO 1
<211> LENGTH: 34
<212> TYPE: PRT
<213> ORGANISM: Lactococcus sp.
<220> FEATURE:
<221> NAME/KEY: MOD_RES
<222> LOCATION: (2)..(2)
<223> OTHER INFORMATION: dehydrobutyrine
<220> FEATURE:
<221> NAME/KEY: THIOETH
<222> LOCATION: (3)..(7)
<223> OTHER INFORMATION: thioether between residues 3 and 7 forming
      lanthionine
<220> FEATURE:
<221> NAME/KEY: MOD_RES
<222> LOCATION: (5)..(5)
<223> OTHER INFORMATION: dehydroalanine
<220> FEATURE:
<221> NAME/KEY: MOD_RES
<222> LOCATION: (8)..(8)
<223> OTHER INFORMATION: Abu
<220> FEATURE:
<221> NAME/KEY: THIOETH
<222> LOCATION: (8)..(11)
<223> OTHER INFORMATION: thioether between residues 8 and 11 forming
      beta-methyllanthionine
<220> FEATURE:
<221> NAME/KEY: THIOETH
<222> LOCATION: (13)..(19)
<223> OTHER INFORMATION: thioether between residues 13 and 19 forming
      beta-methyllanthionine
<220> FEATURE:
<221> NAME/KEY: MOD_RES
<222> LOCATION: (13)..(13)
<223> OTHER INFORMATION: Abu
<220> FEATURE:
<221> NAME/KEY: THIOETH
<222> LOCATION: (23)..(26)
<223> OTHER INFORMATION: thioether between residues 23 and 26 forming
      beta-methyllanthionine
<220> FEATURE:
<221> NAME/KEY: MOD_RES
<222> LOCATION: (23)..(23)
<223> OTHER INFORMATION: Abu
```

-continued

```
<220> FEATURE:
<221> NAME/KEY: THIOETH
<222> LOCATION: (25)..(28)
<223> OTHER INFORMATION: thioether between residues 25 and 28 forming
      beta-methyllanthionine
<220> FEATURE:
<221> NAME/KEY: MOD_RES
<222> LOCATION: (25)..(25)
<223> OTHER INFORMATION: Abu
<220> FEATURE:
<221> NAME/KEY: MOD_RES
<222> LOCATION: (33)..(33)
<223> OTHER INFORMATION: dehydroalanine

<400> SEQUENCE: 1

Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala Asn Ala Ser Ile His Val
            20                  25                  30

Xaa Lys
```

METHOD TO REDUCE CONTAMINATION WHEN CULTURING MYCOBACTERIA

CROSS-REFERENCE TO RELATED APPLICATION

This invention claims the benefit pursuant to 35 U.S.C. §119(e) of U.S. provisional patent application 60/617,008, which was filed Oct. 8, 2004.

FIELD OF THE INVENTION

The present invention relates generally to a method of culturing mycobacteria. Specifically, a method of culturing *Mycobacteria* in the presence of a lantibiotic, resulting in reduced bacterial contamination, is disclosed.

BACKGROUND OF THE INVENTION

*Mycobacteria* are gram-positive, acid-fast rods that do not produce flagella, capsules or spores and do not grow on ordinary microbiological media. They are strict aerobes with nutritionally-exacting growth requirements, typically requiring an enriched medium for culturing. *Mycobacteria* comprise both slow-growing and fast-growing species. Fast-growing organisms, forming colonies in <7 days, are generally regarded as non-pathogenic. The slow-growing organisms, however, are those of clinical interest, as they are causal agents of some chronic infections, including human tuberculosis (*M. tuberculosis*), non-human tuberculosis (*M. bovis*), leprosy (*M leprae*) and Johne's Disease (*Mycobacterium avium* subsp. *paratuberculosis*; MAP).

Because of the slow growth rate and the need for an enriched medium for mycobacterial growth in culture, detection of *Mycobacteria* from clinical samples (e.g. sputum, lung fluids, tissue or feces) represents a significant biological challenge. The challenge arises from the fact that more rapidly-growing bacteria can overgrow the slow-growing mycobacterial organism of interest, thus precluding or significantly hindering *Mycobacteria* detection. Over the decades, several techniques have been developed to decontaminate diagnostic samples (i.e. kill or inhibit non-mycobacterial organisms) submitted for mycobacterial identification. These techniques either kill the potential contaminates or injure them to the extent that their growth is inhibited or totally prevented. For *M. tuberculosis*, for instance, one decontamination process involves processing the sample in 4% sodium hydroxide for several hours, then neutralizing the sodium hydroxide with oxalic acid. After neutralization, a potent cocktail of antibiotics referred to as PANTA (polymyxin B, amphotericin B, nalidixic acid, trimethoprim and azlocillin) is added to the sample to further reduce the growth of contaminating bacteria.

For MAP, one decontamination method involves a three-day protocol that includes processing samples with 0.9% hexadecylpyridinium chloride (HPC; a detergent), centrifuging them and then a double incubation with BHI (brain heart infusion) and antibiotic brew (ANV; amphotericin B, nalidixic acid and vancomycin). Unfortunately, while the MAP decontamination procedures are effective, MAP colony forming unit (cfu) counts are reduced as a result of the decontamination procedure. Most experts agree that a reduction of 1–2 logs of MAP is a typical result of such processing. This reduction potentially lengthens the duration of culturing necessary to detect mycobacterial growth, or in the worse case, renders the *Mycobacteria* non-detectable. Neither outcome is desirable.

Olstein et al. (U.S. patent publication 2003/0175207) disclose the use of bacteriocin-metal complexes for use in detecting bacteria, including mycobacteria, in samples. Imboden et al. (U.S. patent publication 2005/0014932) disclose the use of fusion proteins comprising a bacteriocin as biocides to kill pathogens, including mycobacteria. Neither reference discloses methods of mycobacterial cultures with reduced contamination.

In light of these findings, it is clear that, prior to the present invention, there was an unmet need in the art for a method of culturing *Mycobacteria* that reduces non-mycobacterial contamination, without significantly effect on the *Mycobacteria*. The instant invention meets this need.

SUMMARY OF THE INVENTION

The present invention provides a method for culturing *Mycobacteria* in the presence of a class A lantibiotic, thereby inhibiting or reducing bacterial contamination in the culture by bacteria other than *Mycobacteria*, without significantly disadvantageously affecting or retarding mycobacterial growth. The exemplified lantibiotic is nisin, and the exemplified *Mycobacteria* is *Mycobacterium avium* subsp. *paratuberculosis*, particularly as tested with regard to Johne's disease (also called paratuberculosis), an incurable, chronic, infectious, granulomatous enteritis of ruminants, and occasionally other species. It is most common in cattle and goats and, to a lesser extent, sheep.

Most cattle are infected with Johne's disease at, or soon after, birth through contaminated feed, colostrum, milk, contaminated bedding and water. As the disease progresses, the causative organism (*M. paratuberculosis*) is often shed in large numbers in the feces for long periods of time. It can survive for up to one year in fecal material, depending on the environmental and soil conditions.

It is also an object of the invention to provide a method of detecting *Mycobacteria* in a biological sample, wherein the method comprises culturing the sample in a medium comprising a class A lantibiotic, such as nisin, in an amount sufficient to inhibit bacterial contamination, and then detecting the presence of the *Mycobacteria*. The biological sample can include a range of materials, such as, fecal matter, bronchial lavage, a bodily fluid, gastric aspirate, biopsy material, lymph node, wound swab, and composite fecal samples.

It is a further object of the invention to provide a mycobacterial culture having a reduced level of contamination, as compared with culture samples that have not been treated by the methods provided herein. Kits useful in practicing the methods of the invention are also provided.

It is a yet another object of the invention to provide a method of diagnosing a mycobacterial infection in a subject. Such a method comprises culturing a biological sample from the subject suspected of having such a mycobacterial infection in a medium comprising a class A lantibiotic in an amount sufficient to inhibit bacterial contamination, and then assessing the presence or absence of *Mycobacteria* in the culture, wherein the presence of *Mycobacteria* indicates a mycobacterial infection in the subject.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

DETAILED DESCRIPTION OF CERTAIN PREFERRED EMBODIMENTS

The methods of the instant invention for culturing *Mycobacteria* with reduced contamination can be practiced with any *Mycobacteria* that can be cultured. Such *Mycobacteria* include, but are not limited to, *Mycobacterium tuberculosis* (the causative agent of tuberculosis in humans), *Mycobacterium avium, Mycobacterium avium* subsp. *paratuberculosis* (MAP; causative agent of Johne's Disease in cattle), and *Mycobacterium bovis* (major causative agent of tuberculosis in cattle and other animals).

The methods of the invention may be practiced using any sample suspected of containing a *Mycobacteria*. Such samples include, but are not limited to, any biological sample from a subject that is susceptible to mycobacterial infection. The subject is preferably an animal, more preferably a mammal, and more preferably still, a ruminant, such as cow, sheep, llama, camel, goat, farmed deer, bison, a cloned ruminant, or any other domesticated ruminant or wild ruminant. The most preferred ruminants are cattle, sheep and goats.

Any biological material known to harbor *Mycobacteria* can be used as the biological sample in the methods of the instant invention. Non-limiting examples of biological material useful in the invention include fecal matter, bronchial lavage, bodily fluid such as sputum, milk, urine, cerebrospinal fluid (CSF), pleural fluid, ascitic fluid, synovial fluid and pericardial fluid, gastric aspirates, biopsy material, lymph nodes, muscle tissue, and wound swabs. To assess MAP at the farm level, the biological sample can be a composite fecal sample from a barnyard environment. Advantageously, these composite fecal samples, which are essentially relatively-fresh bovine, manure samples taken from a barnyard and thereby containing fecal matter from more than one animal, are much easier to obtain. Since, for instance, many cows are in one group, a few composite manure samples will effectively reflect MAP infection for the group of cows.

Biological samples can optionally be processed prior to culturing using known processes intended to reduce bacterial contaminantion. The skilled artisan is familiar with various methods of processing. See, e.g., Dundee et al., *Letters in Applied Microbiology* 33 (3): 173–177 (2001), Thornton et al., *J. Clin. Microbiol.* 40(5):1783–90 (2002), and Crossley et al., *Vet. Microbiol.* 107: 257–263 (2005). A preferred method for processing fecal matter, including composite fecal matter, is the Cornell modified decontamination and inoculation methods (Whitlock et al., "Fecal Culture Protocol for *Mycobacterium paratuberculosis*: a recommended procedure" In: *Proceedings of the 94th U.S. Animal Health Association*, Denver, Colo., pp. 280–285 (1994)).

Briefly, 2 grams of fecal matter, obtained from the rectum of a cow, is placed into 35 ml of sterile water and a suspension is made by a vigorous mixing step followed by mechanical rocking for at least 30 minutes. After rocking, the sample is left unmoved at room temperature for 30 minutes to allow larger particulate debris to settle; *Mycobacteria* remain in the liquid portion. For the first decontamination step, 5 ml of the liquid portion (~0.28 gr of fecal sample) is diluted into 25 ml of 0.9% hexadecylpyridinium chloride (HPC) in Brain Heart Infusion broth (BHI); final concentration was ½ strength BHI and 0.75% HPC. This solution is then incubated overnight (about 18 to about 24 hours) at 35 to 37° C. The solution is then centrifuged at 800×g for 30 minutes to pellet the *Mycobacteria*. The supernatant is discard and the pellet is resuspended by vortexing in 1 ml of antibiotic brew (final volume about 1.2 ml) for the second decontamination step, which is an overnight incubation at 35 to 37° C. After this processing procedure, tubes of Herrold's Egg Yolk Media (HEYM) are inoculated with 0.25 ml of the bacterial suspension and are incubated in a slanted position and with caps loose at 37° C. until the surface of the medium was dry. In 1–2 weeks, the caps are tightened and the tubes are put into an upright position for the duration of the culturing. The remaining bacterial suspension can be stored at −70° C.

Lantibiotics

Figure 1:
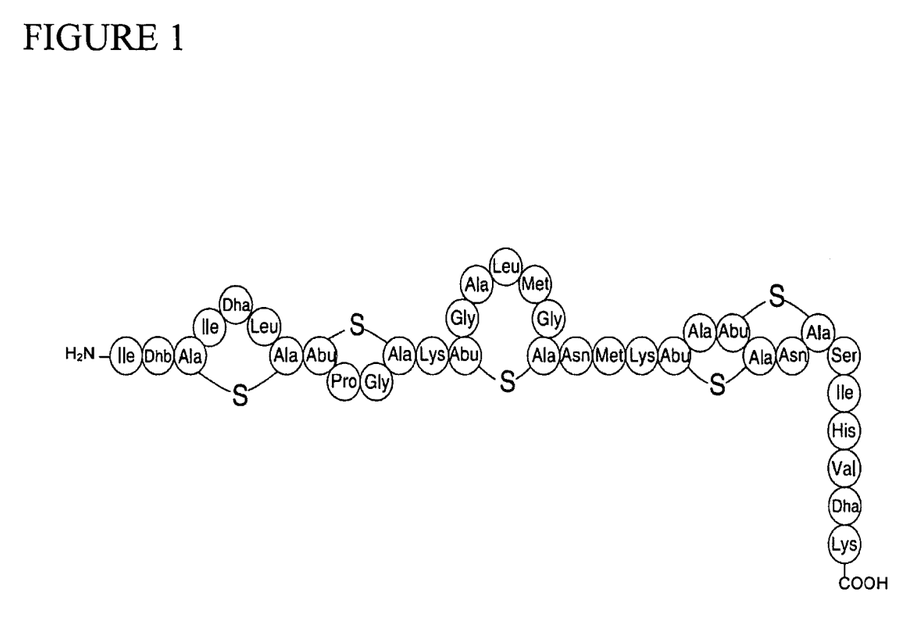
FIG. 1 depicts the sequence (SEQ ID NO. 1) of the lantibiotic, nisin Z, illustrating its unusual amino acids and cyclic bonds. Dha=dehydroalanine. Dhb=dehydrobutyrine. Abu=aminobutryic acid. Ala-S-Ala=lanthionine. Abu-S-Ala=beta-methyl-lanthionine.

Bacteriocins are bacterial, ribosomally-synthesized, antimicrobial polypeptides. Lantibiotics are a type of bacteriocins. Lantibiotics are post-translationally modified peptides, usually less than about 5 kDa, that contain unusual amino acids, including lanthionine and beta-methyl-lanthionine. Specifically, serine and threonine residues of a lantibiotic precursor molecule are dehydrated to dehydroalanine (Dha) and dehydrobutyrine (Dhb), respectively. The resultant alpha, beta-unsaturated residues may then undergo Michael addition reactions with the thiol group of specific cysteine residues to form lanthionine and beta-methyl-lanthionine. See FIG. 1. The presence of these unusual amino acids is a characteristic feature of these peptides. Sahl et al. (*Ann. Rev. Microbiol.* 52:41–49 (1998)) have reviewed these and other characteristics of lantibiotics.

Class A lantibiotics act against target organisms by membrane binding and pore formation, causing leakage of target cell membranes. This mechanism is at least partially voltage dependent. Without wishing to be bound by theory, it is believed that the selective inhibition/killing of non-mycobacterial contamination observed herein is related to the lipid-rich cell wall of mycobacteria.

As used herein a "class A lantibiotic" includes, but is not limited to, nisin, lacticin 481, camocin U149, subtilin, epidermin, pep5, gallidermin, epilancin K7 and lactocin S, fusion proteins thereof, mixtures thereof and fragments, homologs and variants thereof. It is intended that the foregoing and all similar lantibiotic structures are encompassed by the present invention. For example, a truncated lantibiotic or a mutant having a slightly different amino acid sequence may also function adequately in the methods of the invention, provided they possess selective inhibition/killing of bacterial contamination in mycobacterial cultures, and thus, they are included within the invention as described herein.

As used herein, "bacterial contamination" refers to any non-mycobacterial bacteria present in a mycobacterial culture.

Nisin, a 34 amino acid pentacyclic peptide (FIG. 1) produced by *Lactococcus lactis*, and fragments, variants, fusion protein and homologs thereof, is exemplified in the methods of the present invention. Nisin A and nisin Z are preferred in the methods of the invention.

As used herein, the term "fragment" refers to a portion of a lantibiotic that has been enzymatically or chemically truncated or cleaved. Such a fragment may encompass any portion of the native amino acid sequence of the lantibiotic.

The term "variant" refers to a natural or genetically engineered variation in amino acid sequence relative to the native lantibiotic amino acid sequence, such as one, two, three or more amino acid substitutions, deletions, or additions, natural allelic variants, or variations in post-translational processing. Nisin A and nisin Z are natural variants of each other. Nisin A has histidine at position 27, whereas nisin A has an asparagine. The fragments and variants that are useful in the methods of the invention are those that possess the function of selectively inhibiting bacterial contamination in mycobacterial cultures. Such fragments and variants are, therefore, encompassed by the invention.

A wide variety of nisin and related lantibiotic variants have been studied. See, for instance, Kuipers et al., *J. Biol. Chem.* 267:24340–24346 (1992), Breukink et al., *Biochem.* 37:8153–8162 (1998), Van Kraaj et al., *Eur. J. Biochem.* 247:114–120 (1997) and Kuipers et al., *Antonie van Leeuwenhock* 69:161–170 (1996). Studies have shown that the Dhb residues in the central portion of Pep5 appear to stabilize the three-dimensional conformation of this peptide. If Ala is substituted for Dhb, the antibacterial activity is lost. Subtilin may be made more stable by substituting Glu4 for Ile. Similarly, nisin has been engineered to be more stable (Dha5Dhb nisinZ) or more soluble (N27K nisin Z, H31K nisin Z). Gallidermin may be made more stable to trypsin (Dhb14Por A21L) and Pep5 may be made more stable to chymotrypsin (A19C Pep5). T2S nisin Z, L6V gallidermin and M17Q/G18T nisin Z show an enhanced antibacterial activity when used with at least some strains. Therefore, it is clear that variations in the amino acid sequences and post-translational processing of nisin and related peptides are possible. All such variations possessing the function of selectively inhibiting bacterial contamination in mycobacterial cultures are considered to be within the scope of the present application.

The term "homolog" refers to a lantiobiotic having an amino acid sequence homologous to the amino acid sequence of the lantiobiotics discussed herein, and which possesses the function of selectively inhibiting bacterial contamination in mycobacterial cultures. Such homologous sequences are obtained from natural nucleic acid sequences (e.g., genomic DNA, cDNA), as well as synthetic or mutagenized sequences, by performing hybridization experiments under stringent conditions, wherein the nucleic acid sequences encoding homologs hybridize to DNA sequences encoding the amino acid sequence for a particular lantiobiotic. The DNA sequences for lantiobiotics are available to the skilled artisan in the prior art. For example, homologs to nisin are generally peptides whose nucleic acid sequence hybridizes to the nucleic acid sequence for nisin under stringent conditions. Such homologs would be expected to comprise an amino acid sequence that is approximately at least about 50%, preferably at least about 80%, more preferably still at least about 90% to about 99.9%, and most preferably at least about 95% to about 99.9% homologous with that of the native amino acid sequence for nisin, and to exhibit similar structural and functional characteristics. Similarly, other lantiobiotics will have homologs comprising amino acid sequences that are approximately at least about 50%, preferably at least about 80%, more preferably still at least about 90% to about 99.9%, and most preferably at least about 95% to about 99.9% homologous with that of their respective native amino acid sequences. All such homologs would also be expected to be useful in the inventive methods.

The term "stringent conditions" as used herein refers to hybridization performed using buffer containing relatively low salt and/or high temperature conditions, such as provided by 0.02M–0.15M NaCl at temperatures of 50° C. to 70° C. Such selective conditions tolerate little mismatch between the probe and the template or target strand, and would be particularly suitable for isolating homologous genes from related species or mutated genes.

Engineered variants, such as fusion proteins, can also be utilized in the present invention. A particularly preferred embodiment is a fusion protein comprising multiple copies of a lantiobiotic. A preferred lantiobiotic for constructing a multimer of lantiobiotics is nisin. In some instances, the fusion construct is a multimer of one particular lantiobiotic. In other instances, the fusion construct is a multimer of different lantiobiotics. Spacer sequences comprising an amino acid sequence of between about 5 to about 25 amino acids, preferably between about 1 to about 10 amino acids, may be included between the C-terminus of one subunit of lantiobiotic and the N-terminus of the next lantiobiotic.

Standard amino acid residues in peptides are abbreviated as recognized in the art. Conservative amino acid changes may be made, which although they alter the primary sequence of the protein or peptide, do not normally alter its function. In general, conservative replacements are preferred, in which an original amino acid is replaced by an amino acid that resembles the original in one or more of its characteristic properties (e.g., charge, hydrophobicity, steric bulk). Conservative amino acid substitutions typically include substitutions within the following groups: glycine, alanine; valine, isoleucine, leucine; aspartic acid, glutamic acid; asparagine, glutamine; serine, threonine; lysine, arginine; phenylalanine, tyrosine.

In addition, any of the amino acids may be replaced by a non-conventional amino acid, including D amino acids. Modifications, such as acetylation, carboxylation and phosphorylation, of a lantiobiotic are also useful in the instant invention. Any such fragments, of variants of or modified lantiobiotics are embraced by the instant invention provided the function of selective inhibition or killing of contamination in a mycobacterial culture is maintained.

The peptides used in the inventive methods can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides.

In the methods of the invention, the class A lantibiotic is added to the culture medium at a concentration sufficient to inhibit growth of bacterial contamination. As used herein, "inhibiting bacterial contamination" is the reduction of bacterial contamination observed in a *Mycobacteria* sample cultured with a lantiobiotic compared to the bacterial contamination observed in the same *Mycobacteria* sample cultured under the same conditions but without a lantiobiotic. Bacterial contamination in the sample cultured with a lantiobiotic is reduced (inhibited) at least about 10%, preferably at least about 25 to about 50%, more preferably at least about 50% to about 75% and most preferably at least about 90%, as compared to the same sample cultured under the same conditions in the absence of the lantiobiotic. The class A lantiobiotic is added at a concentration of about 500 microgram (μg) per 8.9 milliliter (ml) liquid medium to about 50,000 μg per 8.9 ml liquid medium, more preferably about 5000 μg per 8.9 ml liquid medium to about 25,000 μg per 8.9 ml liquid medium, and most preferably, about 7,500 μg per 8.9 ml liquid medium to about 12,500 μg per 8.9 ml liquid medium. In a preferred embodiment, nisin is added to the culture medium at a concentration of about 10,000 µg per 8.9 ml liquid medium.

The class A lantibiotic can also be added to one of the sample processing steps that typically precede culturing in a liquid medium. For instance, nisin can be used instead or, or in addition to, the antiobiotic brew used in the final decontamination step of the fecal matter processing procedure. Using a lantibiotic at this step is advantageous as the amount used is significantly smaller overall than compared to liquid culture. As described elsewhere herein, sample processing typically involves at least one incubation step in the presence of antiobiotics. The class A lantibiotic can be added to the antiobiotic brew or can replace it. The use of a lantibiotic in a sample processing step can be done instead of or in addition to the liquid culture. In any case, the skilled artisan, armed with this disclosure, can readily assess, without undue experimentation, the optimal concentration for practicing the methods of the invention using any class A lantibiotic and any culture medium.

Methods of Culturing *Mycobacteria*

Methods of culturing *Mycobacteria* are known to the skilled artisan (see, e.g. *Mycobacterium Protocols*, Edited by Tanya Parish and Neil G. Stoker, *Methods in Molecular Biology*, Vol. 101, Humana Press, Totowa, N.J., (1998)). Any mycobacterial culture method can be used in the instant invention.

Any culture medium known to the skilled artisan as suitable for culturing a mycobacterium cell can be used in the method of the invention (see, e.g., Metchock, et al., *Mycobacterium*, p. 399–437. In Murray et al., (eds.), *Manual of Clinical Microbiology*. American Society for Microbiology, Washington, D.C. (1999)). Non-limiting examples of suitable culture medium include 7H12B, 7H9, 7H10, 7H11, Herrold's egg yolk media (HEYM), Sauton's medium (Sauton, C. R. Acad. Sci. 155:860 (1912)), Dubos medium, egg-based medium, Ogowa, blood agar, and Lowenstein-Jensen (L-J) medium. HEYM is the preferred medium for culturing MAP on agar and 7H9 is the preferred medium for liquid culturing of MAP. Growth enhancers can optionally be added to the culture medium. Non-limiting examples of growth enhancers include egg yolk suspension, asparagines, OADC, OACC, special protein hydrolasates, such as peptones, polyoxyethelene stearate (POES), iron-binding hydroxamate compounds (mycobactins) and U.S. Pat. No. 6,664,096 a cell extract from *Mycobacterium tuberculosis* complex (U.S. Pat. No. 6,664,096). In a preferred embodiment, the culture medium has about 500 to 1,200 ul of 50% egg yolk per 8.3 ml of liquid culture medium and for solid media, about 120 ml of egg yolk per liter of HEYM. However, a synthetic medium, providing all the necessary components for growth and therefore not requiring any additional growth enhancers is within the scope of the invention.

A common method of detecting growth in mycobacterial cultures involves the use of oxygen-sensitive luminescent compounds. Examples of luminescent oxygen-sensing particles useful in the methods of the invention include, but are not limited to, any salt of tris-4,7-diphenyl-1,10-phenanthroline ruthenium(II), any salt of tris-2,2'-bipyridyl-ruthenium (II), any salt of tris-1,7-diphenyl-1,10 phenanthroline ruthenium(II), and 9,10-diphenyl anthracene. Luminescent particles can also include platinum(II) octaethyl porphyrin complexes, palladium (II) octaethyl porphyrin complexes, palladium-meso-tetra(4-carboxyphenyl) porphine, palladium-meso-tetra(4-carboxyphenyl) porphyrin dendrimer and palladium-meso-tetra(4-carboxyphenyl) tetrabenzoporphyrin dendrimer.

Examples of salts of tris-4,7-diphenyl-1,10-phenanthroline ruthenium(II) include, but are not limited to, tris-4,7-diphenyl-1,10-phenanthroline ruthenium(II) dichloride pentahydrate, tris-4,7-diphenyl-1,10-phenanthroline ruthenium (III) trichloride, tris-4,7-diphenyl-1,10-phenanthroline ruthenium(II) diperchlorate and tris-4,7-diphenyl-1,10-phenanthroline ruthenium hexafluorophosphate. An example of a salt of tris-2,2'-bipyridyl-ruthenium(II) includes, but is not limited to, tris-2,2'-bipyridyl-ruthenium (II) chloride hexahydrate. An example of a salt of tris-1,7-diphenyl-1,10 phenanthroline ruthenium(II) includes, but is not limited to, tris-1,7-diphenyl-1,10 phenanthroline ruthenium(II) dichloride. In a preferred embodiment, the oxygen-sensitive luminescent compound is a salt of tris-4,7-diphenyl-1,10-phenanthroline ruthenium(II).

Other methods of detecting growth are known to the skilled artisan and include detecting pressure changes and use of a tritiated isotope. Any such methods are also useful in the practice of the invention.

Methods of Assessing *Mycobacteria* Presence

Any method known to the skilled artisan for identifying *Mycobacteria* can be used in the practice of the methods of the instant invention. See, e.g., Parish et al. (eds, 1998, *Mycobacterium Protocols, Methods in Molecular Biology*, Vol. 101, Humana Press, Totowa, N.J.), Sambrook et al. (2001, *Molecular Cloning: A Laboratory Manual*, Cold Spring Harbor Laboratory Press, Cold Spring Harbor, N.Y.), Ausubel et al. (eds., 1997, *Current Protocols in Molecular Biology*, John Wiley & Sons, New York), and Gerhardt et al. (eds., 1994, *Methods for General and Molecular Bacteriology*, American Society for Microbiology, Washington, D.C.). Such methods include, but are not limited to, acid-fast staining, nucleic acid assays, immunoassays, differential growth assays and reporter molecules.

One of the most distinctive properties of *Mycobacteria* is the impermeability of their lipid-rich cell walls to various basic dyes, unless the dye is combined with phenol. Once stained, the cells resist decolorization with acidified organic solvents, and are, therefore called "acid fast." Acid fast staining methods include, but are not limited to, Ziehl-Neelsen (ZN) carbolfuchsin staining, fluorochrome staining (auromine O and rhodamine B) and Kinyoun carbolfuchsin staining.

Nucleic acid assays include, but are not limited to, PCR-based identification, microarray analysis, and hybridization techniques. Nucleic acid assays rely on sequence information of the *Mycobacteria* of interest. Such information is known to the skilled artisan. For instance, a functional genomic analysis of MAP has been undertaken that included identification of MAP specific proteins and their expression and immunogenicity (Bannantine et al., *J. Clinical Microbiol.* 42:106–114 (2004) and Paustian et al., *J. Clinical Microbiol.* 42:2675–2681 (2004). Novel insertion elements have been identified and can be used as the basis of a nucleic acid assay (Strommenger et al., *FEMS Microbiology Letters* 196 (1): 31–37 (2001)). Such information is useful in both nucleic acid assays, including PCR-based identification methods, as well an immunoassays. Genomic sequence is available for *M. bovis* (Garnier et al., *PNAS* 100(13):7877–82 (2003)) and *M. tuberculosis* (Cole et al., *Nature* 393:537–544 (199 Numerous variations of PCR-based assays are known to the skilled artisan. See, e.g., Englund et al., *Veterinary Microbiolog.* 81 (3): 257–271

(2001) and Mason et al., *Australian Veterinary Journal* 79 (7): 497–500 (2001). A rapid method of DNA extraction from fecal matter has been developed (Stabel et al., *J. Vet. Diagn. Invest.* 16(1):22–30 (2004)). Pulsed-field gel electrophoresis can also be used (see, e.g., Hughes et al., *J. Microbiol. Methods* 44 (3): 209–215n (2001)). DNA probes methods are also useful in the instant invention (see, e.g., Dimareli et al., *Australian Veterinary J* 79 (1): 47–50 (2001)).

Flow cytometry has recently been shown to be a rapid, sensitive, and specific method for identifying *Mycobacteria* (Eda et al., *Foodborne Pathog. Dis.* 2(3):250–62 (2005)). Thin layer chromatography can also be used (Leite et al., *Mem. Inst. Oswaldo Cruz*, Rio de Janeiro 93:801–805 (1998)).

Immunological assays useful in the present invention include various immunoassays, for example, immunohistochemistry assays, immunocytochemistry assays, ELISA, capture ELISA, sandwich assays, enzyme immunoassay, radioimmunoassay, fluorescent immunoassay, agglutination assays and the like, all of which are known to those of skill in the art. See, e.g., Harlow et al., 1988, *Antibodies: A Laboratory Manual*, Cold Spring Harbor Laboratory Press, Cold Spring Harbor, N.Y.; Harlow et al., 1999, *Using Antibodies: A Laboratory Manual*, Cold Spring Harbor Laboratory Press, Cold Spring Harbor, N.Y. Examples of immunoassays used for *Mycobacteria* are disclosed in U.S. Pat. Nos. 6,599,691 and 6,841,159, Nielsen et al., *J Vet Diagn Invest.* 13 (2) p. 164–166 (2001), Dargatz et al., *J. Am. Vet. Med. Assoc.* 218 (7): 1163–1166 (2001), Dargatz et al., *J. Am. Vet. Med. Assoc.* 219 (4): 497–501 (2001) and Whitlock et al., *Vet Microbiol.* 77(3–4):387–98 (2000).

Enzyme linked immunoadsorbent assays (ELISA) can be used in the methods of the present invention. In an ELISA assay, proteins or peptides are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological sample to be tested in a manner conducive to immune complex (antigen/antibody) formation. Such conditions preferably include diluting the antisera with diluents such as BSA, bovine gamma globulin (BGG), phosphate buffered saline (PBS)/Tween, and the like. These added agents also tend to assist in the reduction of nonspecific background. The layered antisera is then allowed to incubate for greater than about one hour, at temperatures preferably on the order of about 25° to 27° C. Following incubation, the antisera-contacted surface is washed so as to remove non-immuno-complexed material. A preferred washing procedure includes washing with a solution such as PBS/Tween, or borate buffer.

Following formation of specific immunocomplexes between the test sample and the bound antigen, and subsequent washing; the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a biotin or peroxidase-conjugated anti-appropriate-animal IgG for a period of time and under conditions which favor the development of immunocomplex formation (e.g., incubation for about 2 hours at room temperature in a PBS-containing solution such as PBS-Tween).

After incubation with the second tagged antibody, and subsequent to washing to remove unbound material, the amount of label is quantified by incubation with a chromogenic substrate, such as urea and bromocresol purple, or 2,2'-azino-di-(3-ethyl-benzthiazoline-6-sulfonic acid) [ABTS] and hydrogen peroxide ($H_2O_2$), in the case of peroxidase as the enzyme label. Quantification is then achieved by measuring the degree of color generation, e.g., using a visible spectra spectrophotometer.

Differential growth assays can be used to detect MAP in a sample. Specifically, MAP require mycobactin for growth, thus one can identify a mycobacterial culture as MAP if it requires mycostatin for growth. Reporter systems can also be used to identify *Mycobacteria* in the instant invention. For instance, a luciferase reporter assay has been developed (see, e.g., Sasahara et al., *Abstracts of the General Meeting of the American Society for Microbiology* 101: 576 (2001). In addition, species-specific biologics, such as mycobacteriophages, can be used to identify *Mycobacteria* (see, e.g., U.S. Pat. No. 6,300,061).

Kits

The invention further provides kits useful in the practice of the methods of the invention. The kits comprise a medium suitable for culturing *Mycobacteria*, wherein the medium comprises a class A lantiobiotic in an amount sufficient to inhibit bacterial contamination, and an instructional material for the use thereof. As used herein, an "instructional material" includes a publication, a recording, a diagram, or any other medium of expression which can be used to communicate the usefulness of the kit in detecting or culturing a *Mycobacteria*. The instructional material of the kit of the invention may, for example, be affixed to a container which contains the medium or be shipped together with a container which contains the medium. Alternatively, the instructional material may be shipped separately from the container with the intention that the instructional material and the medium be used cooperatively by the recipient. Optionally, the medium provided in the kit can further comprise an oxygen-sensitive luminescent compound. The kits can also contain any other component useful in the practice of the inventive methods including, but not limited to, a culture vessel, such as a capped tube or flask, a luminescence detector, and positive and negative control samples.

The present invention is further described in the following examples. These examples are provided for purposes of illustration only, and are not intended to be limiting unless otherwise specified. The various scenarios are relevant for many practical situations, and are intended to be merely exemplary to those skilled in the art. These examples are not to be construed as limiting the scope of the appended claims. Thus, the invention should in no way be construed as being limited to the following examples, but rather, should be construed to encompass any and all variations which become evident in light of the teaching provided herein.

EXAMPLE

The materials and methods used in the example are now described.

Solutions

Middlebrook 7H9 broth was prepared by suspending 4.7 grams Middlebrook 7H9 dehydrated base (BD Diagnostics, Sparks, Md.) in 900 ml of double distilled water. The solution was autoclaved for 20 minutes at 121° C., and stored in a refrigerator when not in use. A 50% egg yolk suspension was stored in a refrigerator. Nisin was prepared in 1–2 M hydrochloride acid (HCl) at a concentration of 100 mg/ml. ANV cocktail (5 mg/ml) was prepared from the individual antibiotics and stored frozen.

Organism Preparation

Dilutions of MAP ATCC# 700535 were prepared as follows. A working stock vial, at $10^{-2}$, stored at $-70°$ C. freezer, was thawed in a 37° C. incubator. Using individually-wrapped, sterile glass pipettes, a serial dilution series was made in sterile 15 ml conical tubes. One (1) ml of MAP at $10^{-2}$ was diluted into 9 ml of 7H9 medium and mixed well to yield a $10^{-3}$ solution. One ml of this solution was diluted into another tube of 9 ml 7H9 to yield a $10^{-4}$ solution. This process was repeated again to produce a $10^{-5}$ solution. The serial dilutions were plated on HEYM flasks, 100 ul dilution per flask, and placed in an incubator.

Vials of processed fecal field samples, Annabelle, Heide and Meck 42, stored at $-70°$ C., were thawed in a 37° C. incubator. The samples had been previously processed according to the Cornell modified decontamination and inoculation method as described in Whitlock et al., supra (2000).

Preparation of Culture Tubes

Cultures were set up in MGIT™ tubes (BD Diagnostics, Sparks, Md.). MGIT™ tubes contain an oxygen-sensitive fluorescent compound, tris 4,7-diphenyl-1,10-phenanthroline ruthenium chloride pentahydrate, in silicone base that detects growth by increased fluorescence as oxygen consumption in the culture increases. The tubes were barcoded for scanning in a BACTEC™ MGIT™ 960 machine (BD Diagnostics, Sparks, Md.).

Vials of nisin and ANV, stored in a standard freezer, were thawed in a 37° C. incubator. Egg yolk, OADC or OACC (BD Diagnostics, Sparks, Md.) and 7H9, stored in a standard refrigerator, were warmed in a 37° C. incubator. Using sterile pipet tips (autoclaved), components were aliquoted into barcoded MGIT™ culture tubes as follows: OADC or OACC (800 µl); 50% egg yolk suspension (600 µl except for three control tubes having 60 µl. The volume difference in volume made up by 7H9); 7H9; 5 mg/ml ANV (30 µl); 100 mg/ml nisin (quantity determined by desired final concentration); and organism sample (100 µl). 7H9 was added at the quantity needed to bring the final volume of each tube to 8.9 ml, so that the tubes had identical head space. Table 1 summarizes the contents of each tube with respect to sample, nisin and ANV. After all components were added, tubes were tightly capped and inverted three times. The tubes were placed in the MGIT™ 960 machine and scanned in after they registered as unknown at the next hourly reading.

TABLE 1

| Sample | ID | Vol of Nisin 100 mg/ml Stock | Vol of 5 mg/ml ANV stock | Amount of 7H9 to bring vol to 500 ul |
|---|---|---|---|---|
| Additives | 8S | 5 ul | 30 ul | 465 ul |
| Additives | 8F | 5 ul | 30 ul | 465 ul |
| MAP $10^{-3}$ | WP3 | 0 | 0 | 340 ul + 60 ul EY |
| MAP $10^{-4}$ | WP4 | 0 | 0 | 340 ul + 60 ul EY |
| MAP $10^{-5}$ | WP5 | 0 | 0 | 340 ul + 60 ul EY |
| MAP $10^{-3}$ | 1A | 0 | 30 ul | 470 ul |
|  | 1B | 500 ul HCl | 0 | 0 |
|  | 1C | 5 ul | 0 | 495 ul |
|  | 1D | 10 ul | 0 | 490 ul |
|  | 1E | 50 ul | 0 | 450 ul |
|  | 1F | 100 ul | 0 | 400 ul |
|  | 1G | 500 ul | 0 | 0 |
| MAP $10^{-4}$ | 2A | 0 | 30 ul | 470 ul |
|  | 2B | 500 ul HCl | 0 | 0 |
|  | 2C | 5 ul | 0 | 495 ul |
|  | 2D | 10 ul | 0 | 490 ul |
|  | 2E | 50 ul | 0 | 450 ul |
|  | 2F | 100 ul | 0 | 400 ul |
|  | 2G | 500 ul | 0 | 0 |
| MAP $10^{-5}$ | 3A | 0 | 30 ul | 470 ul |
|  | 3B | 500 ul HCl | 0 | 0 |
|  | 3C | 5 ul | 0 | 495 ul |
|  | 3D | 10 ul | 0 | 490 ul |
|  | 3E | 50 ul | 0 | 450 ul |
|  | 3F | 100 ul | 0 | 400 ul |
|  | 3G | 500 ul | 0 | 0 |
| Annabelle | 4A | 0 | 30 ul | 470 ul |
|  | 4B | 500 ul HCl | 0 | 0 |
|  | 4C | 5 ul | 0 | 495 ul |
|  | 4D | 10 ul | 0 | 490 ul |
|  | 4E | 50 ul | 0 | 450 ul |
|  | 4F | 100 ul | 0 | 400 ul |
|  | 4G | 500 ul | 0 | 0 ul |
| Heidi | 5A | 0 | 30 ul | 470 ul |
|  | 5B | 500 ul HCl | 0 | 0 |
|  | 5C | 5 ul | 0 | 495 ul |
|  | 5D | 10 ul | 0 | 490 ul |
|  | 5E | 50 ul | 0 | 450 ul |
|  | 5F | 100 ul | 0 | 400 ul |
|  | 5G | 500 ul | 0 | 0 |
| Meck 42 | 7A | 0 | 30 ul | 470 ul |
|  | 7B | 500 ul HCl | 0 | 0 |
|  | 7C | 5 ul | 0 | 495 ul |
|  | 7D | 10 ul | 0 | 490 ul |
|  | 7E | 50 ul | 0 | 450 ul |
|  | 7F | 100 ul | 0 | 400 ul |
|  | 7G | 500 ul | 0 | 0 |

NOTE:
EY = 50% egg yolk suspension. With the exception of WP3, WP4 and WP5, all of the tubes contained 600 ul EY. Additives are components (e.g. EY, OACC, ANV) added to a tube not containing MAP or a fecal sample; these are control tubes. Additional 7H9 was added to bring the final tube volume to 8.9 ml.

Results

The experiment was designed to test a MAP isolate (ATCC# 700535) at three different concentrations (MAP $10^{-3}$, MAP $10^{-4}$ and MAP $10^{-5}$). Three field samples (processed fecal matter) named Annabelle, Heidi and Meck 42 were also tested in the experiment. Seven conditions were tested for effectiveness against bacterial contamination in mycobacterial cultures: ANV alone, five different nisin concentrations and HCl, the diluent for nisin. Generally, each sample was tested in triplicate for each solution. There were eleven additional control tubes; two tubes for additives (5 µl nisin and 30 µl ANV) and 9 tubes for weekly performance (no ANV and 60 μl 50% egg yolk suspension; WP). The WP tubes were used to monitor test performance and reproducibility over time.

The results from the experiment are summarized in Table 2.

TTP was reached about 2.5 days faster with 600 ul egg yolk. At MAP $10^{-4}$, TTP was reached about 4 days faster. At MAP $10^{-5}$, TTP was reached about 8 days faster. Thus, 600 ul 50% egg yolk suspension enhanced MAP growth with a faster TTP, compared to 60 ul EY.

TABLE 2

| Row | ID | Sample Source | Amount of Nisin | TTP (days) | Acid Fast Results or CFUs |
|---|---|---|---|---|---|
| 1 | 8S | Additives | 500 ug + ANV | 35.5 | |
| 2 | 1A | MAP $10^{-3}$ | (ANV control) | 21.0–21.0–21.1 | Neg 4.5 d |
| 3 | 1B | | (HCl control) | +T1.4–16.5–17.0 | ND |
| 4 | 1C | | 500 ug | 4.0–15.4–15.9 | ND |
| 5 | 1D | | 1000 ug | 16.0–16.6–17.2 | ND |
| 6 | 1E | | 5000 ug | 16.4–17.5–17.6 | ND |
| 7 | 1F | | 10000 ug | 16.9–17.0–19.1 | 4+Pos–4+Pos–ND |
| 8 | 1G | | 50000 ug | 26.3–34.6–44.1 | ND |
| 9 | 2A | MAP $10^{-4}$ | (ANV control) | 24.1–24.5–25.4 | Neg 4 day |
| 10 | 2B | | (HCl control) | +T1.1–5.2–20.3 | ND |
| 11 | 2C | | 500 ug | 19.3–20.6–No gu's | ND |
| 12 | 2D | | 1000 ug | 20.7–20.8–22.6 | ND |
| 13 | 2E | | 5000 ug | 20.9–23.9–24.4 | ND |
| 14 | 2F | | 10000 ug | 23.9–24.3–28.2 | ND |
| 15 | 2G | | 50000 ug | No gu's | ND |
| 16 | 3A | MAP $10^{-5}$ | (ANV control) | 34.6–45.6–No gu's | Neg 14 d |
| 17 | 3B | | (HCl control) | 26.8–28.5–31.0 | ND |
| 18 | 3C | | 500 ug | 24.4–26.6–28.4 | ND |
| 19 | 3D | | 1000 ug | 26.1–28.2–34.2 | ND |
| 20 | 3E | | 5000 ug | 32.4–38.7–2 gu's | ND |
| 21 | 3F | | 10000 ug | 28.3–32.0–37.3 | ND |
| 22 | 3G | | 50000 ug | 45.3–50.2–52.3 | ND |
| 23 | 4A | Annabelle | (ANV control) | +T0.6–+T0.7–+T1.1 | ND |
| 24 | 4B | | (HCl control) | +T0.6–+T0.6–+T0.7 | ND |
| 25 | 4C | | 500 ug | +T2.2–2.4–+T2.5 | ND |
| 26 | 4D | | 1000 ug | +T1.8–+T4.8–+T4.8 | ND |
| 27 | 4E | | 5000 ug | 5.6–+T5.7–+T8.7 | ND |
| 28 | 4F | | 10000 ug | 13.1–13.8–14.0 | 4+Pos–4+Pos–ND |
| 29 | 4G | | 50000 ug | 43.7 (1 tube only) | ND |
| 30 | 5A | Heidi | (ANV control) | +T1.6–29.3–32.1 | ND |
| 31 | 5B | | (HCl control) | +T1.0–+T1.0–+T1.2 | Cfu = 1,1,0,0 |
| 32 | 5C | | 500 ug | 21.9–22.3–28.6 | 4+Pos–4+Pos–ND |
| 33 | 5D | | 1000 ug | 21.0–24.4–27.1 | 4+Pos–4+Pos–ND |
| 34 | 5E | | 5000 ug | 22.5–23.4–27.3 | 4+Pos–3+Pos–ND |
| 35 | 5F | | 10000 ug | 24.8–25.6–27.2 | 4+Pos–ND–ND |
| 36 | 5G | | 50000 ug | No gu's (1 tube only) | ND |
| 44 | 7A | Meck 42 | (ANV control) | +T0.4–+T0.5–+T0.5 | ND |
| 45 | 7B | | (HCl control) | +T0.4–+T0.4–+T0.4 | cfu = TNTC |
| 46 | 7C | | 500 ug | +T2.9–8.9–+T14.3 | ND |
| 47 | 7D | | 1000 ug | 6.2–8.8–14.7 | ND–ND–4+Pos |
| 48 | 7E | | 5000 ug | 10.5–14.5–14.6 | BC–4+Pos–4+Pos |
| 49 | 7F | | 10000 ug | +T1.3–17.6–18.5 | ND–4+Pos–4+Pos |
| 50 | 7G | | 50000 ug | 54.4 (1 tube only) | ND |
| 51 | WP3 | MAP $10^{-3}$ | None (60 ul EY) | 17.6–17.9–18.0 | ND |
| 52 | WP4 | MAP $10^{-4}$ | None (60 ul EY) | 24.0–24.4–25.3 | ND |
| 53 | WP5 | MAP $10^{-5}$ | None (60 ul EY) | 28.6–34.6–36.6 | ND |
| 54 | 8F | Additives | 500 ug | No gu's | ND |

Note:
WP3 = weekly performance tube for MAP $10^{-3}$;
WP4 = weekly performance tube for MAP $10^{-4}$;
WP5 = weekly performance tube for MAP $10^{-5}$.
GU = growth units. These are arbitrary computer-derived units that reflect incremental fluorescence over time; when GU = 75, the tube is considered to be positive for MAP growth. TTP = time to positive. "T" is the threshold positive and indicates a tube that flags as positive in the first few days of culture. The decimal following the "T" is the time in days. For instance, 0.5 is 12 hours. Such tubes are either false positives or contain bacterial contamination. ND = not determined. ANV control contained ANV and no nisin. HCl control was the nisin diluent without any nisin. Except as otherwise indicated, all samples had 600 ul EY. TTP values are reported for each of the three replicate tubes where applicable. CFUs was determined by culturing the same sample inoculum on four HEYM tubes or flasks; the number of cfus in each tube is reported. Acid Fast bacillus were determined using the Ziehl-Neelson method as recommended by the CDC.

A comparison of the data presented in Table 2 for tube pairs WP3 and 1C, WP4 and 2C, and WP5 and 5C demonstrates the effect of egg yolk on MAP growth. At MAP $10^{-3}$, All of the field samples were contaminated and ANV (30 ul of 5 mg/ml) was not sufficient to control contamination in field samples. See data for tubes 4A and 4B, 5A and 5B, 6A and 6B, and 7A and 7B. Furthermore, ANV (30 ul) retarded MAP growth significantly, as the MAP standards exhibited. Compare, for instance, data for tubes 1A and 1B, 2A and 2B, and 3A and 3B. The negative effect of ANV outweighed the observed positive effect of 600 ul EY on MAP growth. Unexpectedly, nisin had little inhibitory effect on MAP growth and thus, the nisin and 600 ul EY combination was even better for MAP growth.

The addition of nisin to cultures controlled non-mycobacterial contamination with little retardation of MAP growth, particularly at 10,000 ug nisin. See, for instance, Annabelle, Cornell 1262 and Meck. Notably, ANV had little efficacy while nisin controlled contamination in very challenging samples, yet promoted MAP growth. Notably, in some cases, nisin at 10,000 ug/tube reduced TTP approximately 30% compared to 30 ul ANV. See data for tubes 3A and 3F. The diluent in which nisin was prepared, HCl, did not control contamination in any of the field samples. See data for tubes 4B, 5B, 6B and 7B. This observation shows that it was the nisin itself which controlled the contamination and not the HCl.

The positive Meck and Annabelle samples (tubes 4F and 7F), which flagged in 14–17 days, were 4+Positive on AFB (acid-fast bacilli smears). These results indicate that TNTC animals (animals with such a high concentration of *Mycobacteria* in the biological sample, it is "too numerous to count"; synonymous with "heavy shedder") can be recovered in fewer than 15 days when 600 ul 50% egg yolk suspension is added to the culture, and the bacterial contamination is controlled by the addition of sufficient amounts of nisin, at approximately 5000 to 10,000 ug per tube.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A method of inhibiting bacterial contamination in a *Mycobacteria* culture, the method comprising culturing the *Mycobacteria* in a medium comprising a class A lantibiotic in an amount sufficient to inhibit bacterial contamination in the *Mycobacteria* culture.

2. The method of claim 1, wherein the class A lantibiotic is selected from the group consisting of nisin, lacticin 481, camocin U149, subtilin, epidermin, pep5, gallidermin, epilancin K7 and lactocin S.

3. The method of claim 2, wherein the class A lantibiotic is nisin.

4. The method of claim 1, wherein the *Mycobacteria* is selected from the group consisting of *Mycobacterium tuberculosis, Mycobacterium avium, Mycobacterium avium* subsp. *paratuberculosis*, and *Mycobacterium bovis*.

5. The method of claim 4, wherein the *Mycobacteria* is *Mycobacterium avium* subsp. *paratuberculosis*.

6. The method of claim 1, further comprising culturing in presence of an oxygen-sensitive luminescent compound.

7. The method of claim 6, wherein the oxygen-sensitive luminescent compound is selected from the group consisting of a tris-4,7-diphenyl-1,10-phenanthroline ruthenium(II) salt, a tris-2,2'-bipyridyl-ruthenium(II) salt, a tris-1,7-diphenyl-1,10 phenanthroline ruthenium(II) salt, and 9,10-diphenyl anthracene.

8. The method of claim 1, wherein the medium comprises no antibiotic compound other than the class A lantibiotic.

9. The method of claim 1, further comprising, prior to culturing, incubating *Mycobacteria* in a class A lantibiotic.

* * * * *